United States Patent [19]

Buysch et al.

[11] Patent Number: 4,633,016
[45] Date of Patent: Dec. 30, 1986

[54] DIPHENYLAMINE AGE RESISTERS FOR RUBBER

[75] Inventors: Hans-Josef Buysch, Krefeld; Josef Witt, Cologne; Zsolt Szentivanyi, Leverkusen, all of Fed. Rep. of Germany

[73] Assignee: Bayer Aktiengesellschaft, Leverkusen, Fed. Rep. of Germany

[21] Appl. No.: 762,850

[22] Filed: Aug. 6, 1985

[30] Foreign Application Priority Data

Aug. 18, 1984 [DE] Fed. Rep. of Germany ....... 3430510

[51] Int. Cl.⁴ ............... C07C 149/41; C07C 149/437; C07C 149/42
[52] U.S. Cl. .................. 564/154; 260/404.5; 564/192; 564/49; 564/162; 564/340; 564/430; 564/434; 560/27; 560/25
[58] Field of Search ........... 564/154, 162, 192; 260/204.5

[56] References Cited

U.S. PATENT DOCUMENTS 3,975,414 8/1976 Kline .................... 564/154

FOREIGN PATENT DOCUMENTS 1441621 7/1976 United Kingdom .

Primary Examiner—Anton H. Sutto
Assistant Examiner—Carolyn S. Greason
Attorney, Agent, or Firm—Connolly and Hutz

[57] ABSTRACT

Compounds corresponding to the general formula

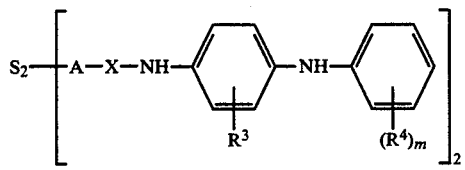

wherein
$R^3$ represents H, $CH_3$
$R^4$ represents H, $C_{1-12}$alkyl, $C_{1-4}$alkoxy, $C_{1-12}$alkylamino, $C_{7-8}$aralkylamino, arylamino, or $C_{7-20}$aralkyl,
A represents a two-bonded group having the structure

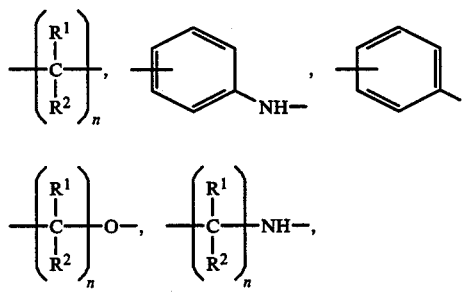

X may represent a single bond or —CO— if it is attached to a carbon atom but only —CO— if it is attached to a hetero atom,
$R^1$ represents $R^2$, H or $C_{1-4}$alkyl,
m represents 1 or 2 and
n represents an integer from 1 to 12 are suitable as age resisters which can be built into polymers, in particular nitrile rubber.

3 Claims, No Drawings

DIPHENYLAMINE AGE RESISTERS FOR RUBBER

This invention relates to compounds corresponding to formula I

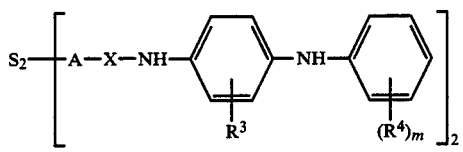

wherein
$R^3$ represents H, $CH_3$,
$R^4$ represents H, $C_{1-12}$-alkyl, $C_{1-4}$alkoxy, $C_{1-12}$alkylamino, $C_{7-18}$aralkylamino, arylamino or $C_{7-20}$aralkyl,
A represents a double bonded group having the structure

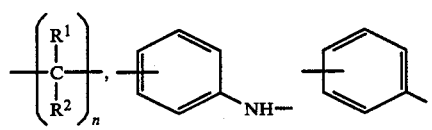

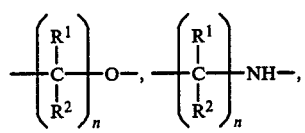

X may represent a single bond or —CO— when it is attached to a carbon atom but only —CO— when it is attached to a hetero atom,
$R^1$ and $R^2$ represent H or $C_{1-4}$alkyl,
m represents 1 or 2 and
n represents an integer from 1 to 12, their preparation, and polymers containing these compounds as age resisters.

Polymers are rapidly changed by the action of light, air and heat and lose their advantageous use properties due to degradation and cross-linking processes. Age resisters are therefore added to polymers to increase their length of life by a considerable amount. The addition of age resisters, however, is in many cases not sufficient when articles of use produced from such polymers come into contact with media which are capable of extracting the age resisters and thus considerably impair or even destroy their protective function. It is also known that age resisters migrate and bleed from the polymer.

It has been proposed to bind the age resister to the polymer in such cases or to use polymeric age resisters.

Thus, according to DE-OS No. 2 735 178, age resisters corresponding to the general formula

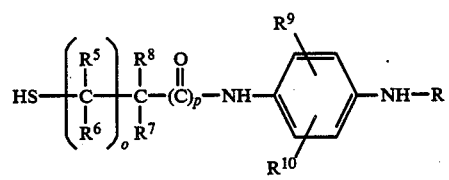

wherein
R may represent inter alia phenyl optionally substituted by $C_1-C_4$ alkyl,
$R^5$-$R^{10}$ represent H or $C_1-C_5$-alkyl,
p represents 0 or 1 and
o has a value from 0 to 12, are linked to the polymer chain.

Although it can be proved that these age resisters are at least partly fixed to the polymer and provide a certain, limited protection against ageing caused by extraction, polymers which have been treated with age resisters in this manner have significantly less age resistance than that obtainable with age resistors based on amines such as distyryldiphenylamine which are not chemically fixed.

Another disadvantage is that they limit the scorch time and hence the time available for processing the polymer compounds containing them.

It was an object of the present invention to provide age resisters which would ensure a sufficient length of processing time as well as providing adequate protection and being capable of being linked to the polymer so that they would remain effective under conditions of extraction.

This problem is solved by compounds corresponding to formula I described above, in which the symbols preferably have the following meanings:
$R^3$=H,
$R^4$=H, $C_{1-12}$alkyl, $C_{1-4}$alkoxy or $C_{7-20}$aralkyl,
A=a divalent group corresponding to one of the following formulae:

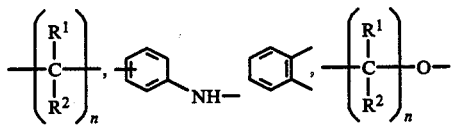

wherein
$R^1$ and $R^2$=H or $CH_3$,
X=—CO—,
m=1 or 2 and
n=an integer from 1 to 5,
the following being particularly preferred:
$R^3$=H,
$R^4$=$C_{7-13}$aralkyl,
A=$(CH_2)_n$, $(CH_2)_n$—O,

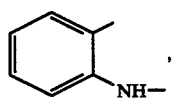

X=CO,
m=1 or 2 and
n=an integer from 1 to 5.

The compounds according to the invention may be prepared by various processes. According to a first process, 4-amino-diphenylamine derivatives corresponding to formula III

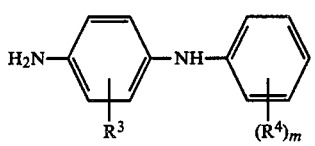

are reacted with compounds corresponding to formula IV $$S_2\text{—}A\text{—}X\text{—}Y]_2 \qquad IV$$

wherein $R^3$, $R^4$, m, A and X have the meaning indicated above and Y represents Cl or $OR^5$, wherein $R^5$ denotes H, $C_{1-4}$alkyl or aryl.

SThe compounds according to the invention may also be prepared by the oxidation of mercapto compounds corresponding to formula V

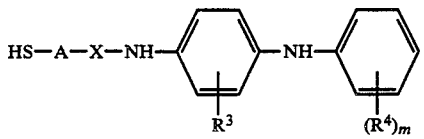

The oxidation of mercapto compounds is carried out by known methods, using halogens, peroxides or atmospheric oxygen.

According to another process, compounds corresponding to formula VI

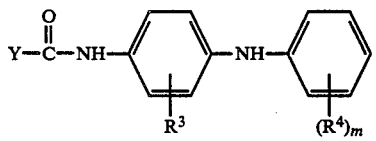

are reacted with compounds corresponding to formula VII $$S_2\text{—}A\text{—}H]_2 \qquad VII$$

in a molar ratio of 2:1.

The compounds according to the invention may be purified by recrystallisation, optionally in the presence of adsorbents. In many cases, this step is unnecessary and the crude products are used.

The new age resisters corresponding to formula (I) may be linked to the polymer by various methods, namely during radical polymerisation of the monomers mentioned below, preferably by addition to the finished polymers but most preferably during hardening and vulcanization of the polymers.

These reactions are carried out by known methods in the presence of compounds I, either solvent-free or in the form of emulsions, solutions or dispersions, and hardening or vulcanization is carried out under the usual conditions and in the presence of known curing and vulcanization systems. The quantity of age resister used ranges from 0.2 to 10% by weight, preferably from 0.5 to 5% by weight, based on the polymer.

The age resisters I according to the invention may also be added at high concentrations to polymers having molecular weights of from 1000 to 30,000 (numerical average), preferably from 2000 to 20,000, so that the polymers contain from 10 to 60% by weight, preferably from 15 to 50% by weight of age resisters linked to them. Compounds of this kind are then added to the high molecular weight polymers and again form migration-resistant, effective polymeric age resisters which are difficult to remove by extraction. They are added to the high molecular weight polymers in such quantities that the total polymer obtained contains the concentrations of age resisters mentioned above. For this purpose, low molecular weight polymers containing the age resister in a chemically bound form are used in quantities of from 1 to 25% by weight, preferably from 4 to 20% by weight, based on the high molecular weight polymer.

The following are examples of suitable low molecular weight polymers for such addition reactions: Polybutadienes, polyisoprenes, copolymers of butadiene and/or isoprene with styrene, acrylonitrile, methyl methacrylate, ethyl acrylate, α-methylstyrene, piperylene, hexadiene-(1,3), ethylene, propylene and vinyl acetate.

Addition of the age resisters to the polymers may be carried out under radical conditions, for example in the presence of known radical starters such as dicumyl peroxide, ditert.-butyl peroxide or azodiisobutyronitrile, but it is preferably carried out purely by heat at temperatures above 100° C., preferably at 120° to 300° C., most preferably at 140° to 280° C., such an addition reaction proceeding smoothly and in high yields.

The new age resisters are suitable for a wide range of rubbers and plastics, especially rubbers, e.g. polymers of 1,3-dienes such as butadiene, isoprene, piperylene, 2-chlorobutadiene, 2-ethyl-butadiene and their copolymers with vinyl monomers such as styrene, p-methylstyrene, α-methylstyrene, norbornene, norbornadiene, acrylic acid, acrylic acid esters and amides, acrylonitrile, ethylene, propylene or vinyl acetate, and for polyalkenamers, e.g. those obtained from cyclopentene or 1,5-cyclooctadiene, and for polymers obtained from 1-olefine mixtures, for example, ethylene/propylene or ethylene/propylene/diene mixtures with isolated double bonds. Polymers of this kind may have been formed by radical, coordinative, metathetic or ionic polymerisation.

Examples of such polymers are: BR, natural rubber, SBR, NBR, EPDM and CR, and polypentenamers; also polyethylene, polypropylene or polystyrene with a low double bond content, and monophasic and polyphasic polymer mixtures such as ABS or polystyrene, polyethylene or polypropylene, but polymers containing double bonds are preferred.

Age resisters are particularly effective in nitrile rubber.

The rubbers may be vulcanized.

A further improvement in the elongation at break may be achieved by the addition of 5 to 15% by weight, based on the rubber solids content, of oligomeric thioethers, e.g. etherthioethers such as Vulkanol 85 ® of Bayer AG, Leverkusen.

EXAMPLE 1

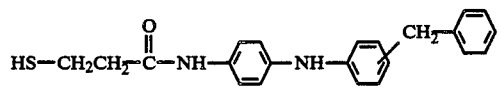

(a) 216 g (2 mol) of benzyl alcohol were added dropwise, with stirring, in the course of one hour to a mixture of 184 g (1.0 mol) of 4-amino-diphenylamine and 20 g of acid-activated Fuller's earth at 200° C. under nitrogen. The temperature was maintained at 200° C. for a further 3 hours, the reaction mixture was filtered through a pressure filter after dilution with toluene, the filtrate was concentrated by evaporation, unreacted starting materials were filtered off under reduced pressure, and finally, 280 g of a fraction containing small quantities of the dibenzyl-substituted compound in addition to benzyl-substituted 4-amino-diphenylamine were distilled off at 230°–260° C./0.6–1.0 mbar.

(b) A mixture of 137 g (about 0.5 mol) of the product obtained from 1a, 53 g (0.5 mol) of β-mercaptopropionic acid and 250 ml of xylene was boiled under reflux in a water separator with stirring under nitrogen until no more water separated. A total of 7.3 ml of water could be separated off. The solution was concentrated by evaporation to a sump temperature of 175° C./10 mbar and thus freed from xylene and unreacted mercaptopropionic acid. 168 g of a brown resin having a SH content of 8.4%, i.e. 92% of the calculated value, were obtained.

EXAMPLE 2

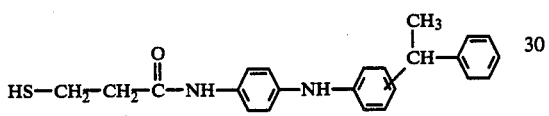

(a) 208 g (2.0 mol) of styrene were added dropwise in the course of 2 hours to a mixture of 184 g (1.0 mol) of 4-amino-diphenylamine and 20 g of acid-activated Fuller's earth with stirring at 200° C. under nitrogen and the mixture was then maintained at 200° C. for a further hour. After dilution with toluene, the reaction mixture was filtered through a pressure filter and the filtrate was distilled under reduced pressure and freed from solvent and unreacted starting materials. 286 g of the required compound finally distilled over at 220°–243° C./0.2–0.3 mbar.

(b) A mixture of 144 g (about 0.5 mol) of the compound from 2a, 53 g (0.5 mol) of β-mercaptopropionic acid and 250 ml of xylene was boiled under reflux in a water separator with stirring under nitrogen until 7.5 ml of water had separated. The solution was then concentrated by evaporation to a sump temperature of 170° C. at 10 mbar. 176 g of a brown resin having a SH content of 8.3%, corresponding to 94% of the calculated value, were obtained.

EXAMPLE 3

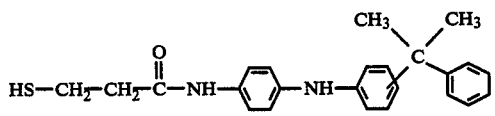

and

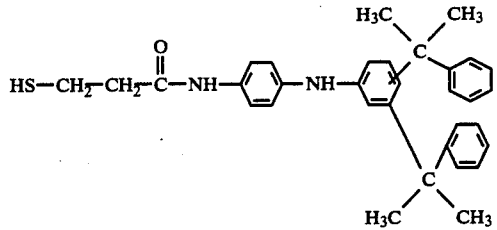

(a) 1025 g (8.7 mol) of α-methylstyrene were added dropwise, with stirring, over a period of 2 hours to a mixture of 800 g (4.35 mol) of 4-amino-diphenylamine and 80 g of acid-activated Fuller's earth at 200° C. under nitrogen, the temperature was maintained at 200° C. for a further hour, the reaction mixture was filtered through a pressure filter after dilution with toluene, and the filtrate was distilled off at reduced pressure, solvent and unreacted starting products distilling off first, followed, at 236°–255° C./0.3 mbar, by a fraction I (787 g) consisting mainly of monoalkylated compounds, and then, at 268°–288° C./0.3–0.5 mbar, by a fraction II (530 g) consisting mainly of the dialkylated compound.

(b) A mixture of 151 g (about 0.5 mol) of fraction I from 3a, 53 g (0.5 mol) of β-mercaptopropionic acid and 250 ml of xylene was reacted until separation of water (8.0 ml) was completed as in 2b and then worked up in analogous manner. A slowly crystallising, brown resin (188 g) having a SH content of 8.4%, equal to the calculated value, was obtained.

EXAMPLE 4

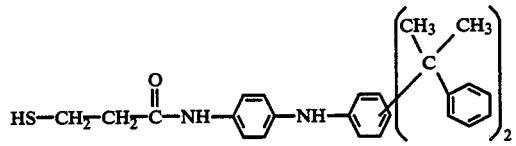

A mixture of 210 g (about 0.5 mol) of fraction II from 3a, 53 g (0.5 mol) of β-mercaptopropionic acid and 300 ml of xylene were reacted together as in 3b. 7.5 ml of water and a dark brown resin having a SH content of 6.1%, corresponding to 97% of the calculated value, were obtained.

EXAMPLE 5

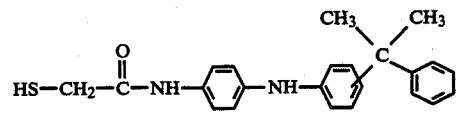

A mixture of 151 g (about 0.5 mol) of fraction I from 3a, 46 g (0.5 mol) of mercaptoacetic acid and 250 ml of xylene was reacted as in 3b, 8.5 ml of water being split off. 188 g of a light brown, slowly crystallising resin having a SH content of 7.8%, corresponding to 89% of the calculated value, were obtained.

EXAMPLE 6

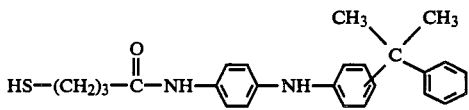

A mixture of 151 g (about 0.5 mol) of fraction I from 3a and 51 g (0.5 mol) of γ-thio-butyrolactone was heated to 140°-150° C. for 5 hours with stirring under nitrogen. The light brown resin formed had a SH content of 7.3%, corresponding to 89% of the calculated value.

EXAMPLE 7

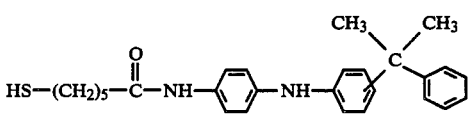

A mixture of 151 g (about 0.5 mol) of fraction I from 3a, 74 g (0.5 mol) of ε-mercapto-caproic acid and 300 ml of xylene was reacted together as in 3b and then evaporated to a sump temperature of 180° C. at 1 mbar to free it from volatile substances. A brown resin having a SH content of 7.3%, corresponding to 95% of the calculated value, was obtained.

EXAMPLE 8

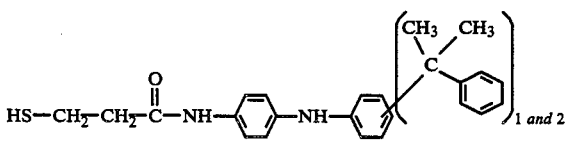

Example 3a was repeated but without fractional distillation of the crude reaction product. Instead, 132 g of the reaction product were directly condensed with 41 g of β-mercaptopropionic acid after removal of unreacted starting materials. A deep brown resin having a SH content of 7.5% was obtained.

EXAMPLE 9

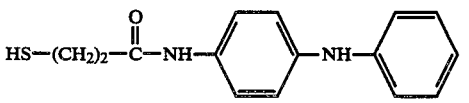

A mixture of 184 g (1 mol) of 4-amino-diphenylamine, 106 g (1 mol) of β-mercaptopropionic acid and 300 ml of xylene was boiled under nitrogen with removal of water until 25 to 30 ml of water had distilled off. After cooling, the reaction mixture was suction filtered and recrystallised from toluene: 151 g, m.p. 96°-98° C., SH content calculated 11.7%, found 11.5%.

EXAMPLE 10

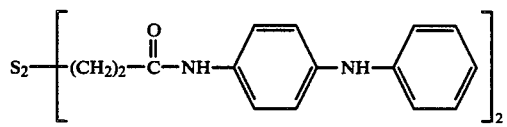

10 g of β-mercaptocarbonamide from Example 9 were dissolved in butanol, 3.2 g of 30% hydrogen peroxide were added, and the reaction mixture was stirred at 50° C. for 8 hours. 7.3 g of product melting at 191°-194° C. were obtained.
S content Calculated 11.7 Found 11.5%.
SH content Calculated 0 Found 0.2%.

EXAMPLE 11

10 g of β-mercaptocarbonamide from Example 9 were dissolved in butanol and gassed with air for 10 hours at 50° C. with stirring. A product melting at 195°-198° C. and having a S content of 11.7% (calculated 11.7%) and
SH content of 0.13% was isolated after cooling.

EXAMPLE 12

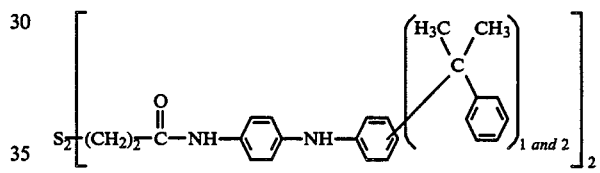

130 g of the product from Example 8 were dissolved in ethanol and 30 g of 45% sodium hydroxide solution were added portionwise with cooling. An ethanolic solution of 38 g of iodine was added dropwise to this solution at 20°-25° C. over a period of 4 hours. After a further 30 minutes, the solution was concentrated by evaporation at reduced pressure, the residue was taken up in water and toluene, the phases were separated and the organic phase was washed with water and concentrated by evaporation. A dark resin having a S content of 6.9% (calculated 7.5%) and a SH content of 0.3% (calculated 0%) was obtained.

EXAMPLE 13

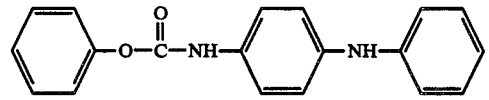

(a) A solution of 150 g (1 mol) of chloroformic acid phenyl ester was added dropwise with stirring over a period of 2 hours to a solution of 184 g (1 mol) of 4-amino-diphenylamine and 110 g (1.10 mol) of triethylamine in toluene at 30°˙ to 40° C. under nitrogen. After a further 4 hours at 30° C., the reaction mixture was suction filtered, thoroughly washed with toluene and then with water, and dried: 241 g (melts with reaction):
(b)

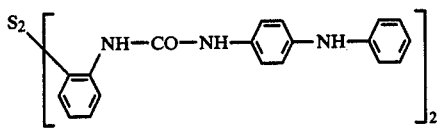

20 g of o,o'-diamino-diphenyldisulphide and 48.8 g of the urethane from 13a were heated to 100° C. in dimethylacetamide for 40 to 50 minutes and the solution was poured into methanol. The dark floccules which separated in the process were removed and water was introduced dropwise into the clear solution. 39 g of pale grey crystals separated. M.p. 119°–122° C.

EXAMPLE 14

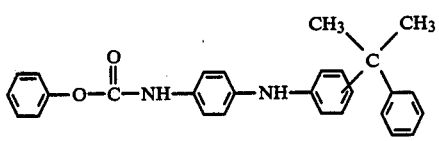

(a) Example 13a was repeated but using the amine from Example 3a, fraction I instead of 4-amino-diphenylamine. According to NMR analysis, the above urethane, m.p. 116°–119° C. was obtained.

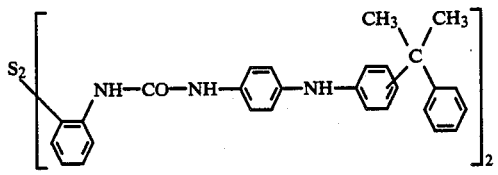

(b) Example (13b) was repeated with the urethane from 14a instead of 13a. According to analysis, the urea corresponding to the above formula was obtained.

EXAMPLE 15

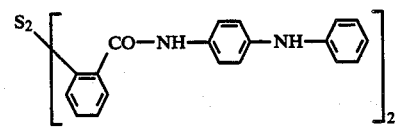

A solution of 45 g (0.13 mol) of dithiosalicyclic acid chloride (prepared from dithiosalicyclic acid and thionyl chloride) in toluene was introduced dropwise at 30°–40° C. over a period of one hour into a solution of 48.6 g (0.264 mol) of 4-amino-diphenylamine and 31.5 g (0.315 mol) of triethylamine in toluene/dimethylacetamide, and the mixture was stirred for a further 2 hours at 30° C. 56 g of crystals, m.p. 225°–226° C., were left after suction filtration and washing with water and toluene.

EXAMPLE 16

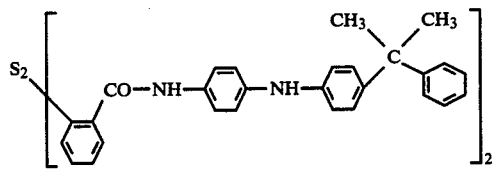

Example 15 was repeated with the amine from Example 3a, fraction I, instead of with 4-amino-diphenylamine. 120 g of a brittle, non-crystalline product were isolated; the analysis of this product did not correspond with the calculated values.

EXAMPLE 17

A mixture of 60% by weight of a NBR oil (molecular weight 1900, 23% acrylonitrile) and 40% by weight of the disulphide-diamide from Example 12 was heated to 230° C. under nitrogen for 10 minutes. The modified oil was purified by triple reprecipitation from toluene/ethanol. The yield of reprecipitated oil was 57%, based on the sum of starting materials. The sulphur content of the reprecipitated, modified NBR oil was 2.9%, corresponding to virtually quantitative linkage of the product from Example 12 to the NBR oil.

EXAMPLE 18

A mixture of 53% by weight of a polybutadiene oil (molecular weight 2100, proportion of 1,4-component 97%) and 47% by weight of the product from Example 14 were reacted as in Example 17 and purified by reprecipitation. The yield of reprecipitated, modified polymer obtained was 70%, based on the sum of starting materials. Its sulphur content was 3.0%, corresponding to approximately 90% linkage of the product from Example 14 to the polybutadiene oil.

EXAMPLE 19

A NBR rubber consisting of 72% butadiene and 28% acrylonitrile was vulcanized in the presence of stabilizers, using the following formulation:

100.00 parts by weight NBR
0.75 parts by weight stearic acid
3.0 parts by weight zinc oxide
1.5 parts by weight mercaptosilane
2.5 parts by weight a mixture of fatty acid and fatty acid esters
30.0 parts by weight precipitated silica
30.0 parts by weight kaolin, calcined
0.25 parts by weight sulphur granulate, 80%
2.5 parts by weight tetramethylthiuramic disulphide
2.0 parts by weight dibenzothiazyl disulphide
4.0 parts by weight zinc salt of mercaptobenzothiazole
10.0 parts by weight thioether
2.0 parts by weight age resister A–D
A=Distyryldiphenylamine
B=Comparison product No. II from the summary on page 15 of DE-OS No. 2 735 178
C=Product from Example 10 according to the invention
D=Product from Example 12 according to the invention

|  | A | B | C | D |
|---|---|---|---|---|
| Mooney Scorch 120° C. (min) | 16.2 | 7 | 15.7 | 15.3 |
| Vulcameter $t_{10}$ (min) | 2.4 | 2.3 | 2.4 | 2.4 |
| 170° C. $t_{70}$ (min) | 3.4 | 3.1 | 4.1 | 3.4 |
| Vulcanization 20' 170° C. | | Standard rod II | | |
| Tensile strength (MPa) | 19.4 | 18.3 | 19.9 | 17.6 |
| Elongation at break % | 585 | 630 | 545 | 565 |
| Hardness RT Shore A | 59 | 55 | 57 | 59 |
| Hot air ageing 150° C. | | cellular furnace 3 and 5 days | | |
| Residual elongation at break after 3 days (%) | 92 | 70 | 81 | 89 |
| Residual elongation at break after 5 days (%) | 63 | 42 | 50 | 59 |
| Ageing in motor fuel C 48 h 40° C., 48 hours redrying at 40° C. under vacuum followed by hot air ageing 135° C., cellular furnace 7 and 11 days | | | | |
| Residual elongation at break after 7 days (%) | 11 | 33 | 66 | 73 |
| Residual elongation at break after 11 days (%) | 4 | 21 | 51 | 60 |

The above results show that (1) Comparison product B according to DE-OS No. 2 735 178 drastically shortens the scorch time compared with the known age resister A.

(2) Products C and D according to the invention produce virtually no shortening of the scorch time compared with A.

(3) The age resistance provided by B is substantially inferior to that of the commercial product A (rapid loss in elongation at break) under conditions of normal hot air ageing, although ageing in motor fuel C followed by hot air ageing shows up advantages of B compared with A.

(4) Products C and D according to the invention approach or virtually reach the age resistance which can be obtained with A under simple hot air ageing. C and D are found to be superior to both A and B under conditions of ageing in fuel followed by hot air ageing. The elongation at break in that case is considerably higher than in B and particularly than in A.

(5) The values obtained for C and D under simple conditions of hot air ageing hardly differ from those measured after ageing by extraction; it must therefore be concluded that a high percentage of the age resister is chemically bound.

The values for B are considerably lower after extractive ageing than after hot air ageing, evidently because a not inconsiderable proportion of the age resister was washed out.

We claim:

1. A compound corresponding to the general formula

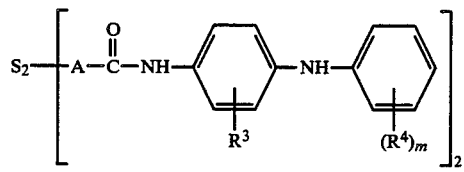

wherein
$R^3$ represents H or $CH_3$,
$R^4$ represents $C_{7-20}$ aralkyl,
A represents a two-bonded group having one of the following structures:

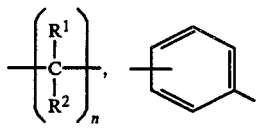

$R^1$ and $R^2$ represent H or $C_{1-4}$ alkyl,
m represents 1 or 2 and
n represents an integer from 1 to 12.

2. A compound according to claim 1, wherein
$R^3$ represents H,
$R^1$ and $R^2$ represent H or $CH_3$ and
n represents an integer from 1 to 5.

3. A compound according to claim 1, wherein
$R^3$ represents H,
A represents $-(CH_2)_n-$, and
n represents and integer from 1 to 5.

* * * * *